United States Patent [19]

Thomas et al.

[11] 4,331,859
[45] May 25, 1982

[54] DEVICE FOR STERILIZING FALSE TEETH

[75] Inventors: Michael D. Thomas; Francis E. Ryder, both of Arab, Ala.

[73] Assignee: Ryder International Corporation, Arab, Ala.

[21] Appl. No.: 211,251

[22] Filed: Nov. 28, 1980

[51] Int. Cl.³ ............................................. H05B 1/02
[52] U.S. Cl. ...................... 219/521; 219/401; 219/441; 219/442; 422/307
[58] Field of Search ............... 219/441, 401, 521, 385, 219/512, 442; 422/307, 105

[56] References Cited

U.S. PATENT DOCUMENTS

| | | | |
|---|---|---|---|
| 1,976,196 | 10/1934 | Sawyer | 219/441 |
| 2,531,180 | 11/1950 | Weeks | 219/441 |
| 2,657,299 | 10/1953 | McNairy | 219/441 |
| 2,761,375 | 9/1956 | Jepson | 219/441 |
| 2,952,764 | 9/1960 | Miwami | 219/441 |
| 3,983,362 | 9/1976 | Hoogesteger et al. | 219/521 |
| 4,044,226 | 8/1977 | Kadlecik et al. | 219/521 |
| 4,158,126 | 6/1979 | Seitz | 219/521 |
| 4,165,359 | 8/1979 | Thomas et al. | 422/105 |
| 4,228,136 | 10/1980 | Thomas | 422/307 |

*Primary Examiner*—Roy N. Envall, Jr.
*Assistant Examiner*—Bernard Roskoski
*Attorney, Agent, or Firm*—Trexler, Bushnell & Wolters, Ltd.

[57] ABSTRACT

There is disclosed a disinfecting unit specifically designed for false or artificial dentures. The unit includes a base providing a cavity, having a support wall partially defined by a heater block. A receptacle for the dentures is provided, which is of sufficient size to accommodate dentures and a quantity of disinfecting solution. The support wall is spaced from the bottom wall of the base to accommodate the circuit and operating components, which include a re-set thermostat and a rockably mounted lever for operation of said re-set thermostat.

3 Claims, 5 Drawing Figures

DEVICE FOR STERILIZING FALSE TEETH

BACKGROUND OF THE INVENTION

This invention relates to sterilizing or disinfecting devices, and more particularly to a device for sterilizing artificial dentures. The cleaning of removable artificial dentures has been a problem and an inconvenience that most users have had to endure, with most existing known procedures utilizing a chemical action. More specifically, the dentures are placed in an effervescent chemical solution, with the bubbling action serving to promote cleaning. While these procedures have proven effective in rendering the dentures more pleasing in relation to replacement in the user's mouth, and to serve to remove food stains and destroy some bacteria, these procedures have not proven sufficiently effective in destorying the major portion of the odor causing bacteria that results from the use of artificial dentures. The present invention provides a unique device which permits the employment of a heat disinfecting operation which will serve more effectively to destory odor causing bacteria, as well as other forms of bacteria.

The device of the present invention is electrically operated and relatively easy to use. It is also compact, and semiautomatic in operation, easy to clean, trouble-free in operation, and heats up and runs through its cycle of operation rapidly without continued user supervision. The unit is also relatively inexpensive and safe in its construction and operation.

OBJECTS AND SUMMARY OF THE INVENTION

An object of this invention is to provide an electrically operated sterilizing device of the type stated and which has the foregoing desired characteristics.

A further object of this invention is to provide a sterilizer of the type stated which embodies a thermostatic control that cuts off the supply of current to the electric heater when the unit reaches a predetermined temperature, and wherein there is a unique, readily accessible mechanism, for re-setting the thermostat for another cycle of operation.

In accordance with the foregoing objects the device comprises a base having an internal or support wall and a surrounding sidewall, said support wall and said sidewall defining a cavity opening at the top of the base, said intermediate or support wall including a heater block for supplying heat to said cavity, and a receptacle for receiving the dentures to be disinfected and a quantity of disinfecting solution and being removable from said cavity, an electric heating element adjacent to said heater block and outside of said cavity, a circuit for supplying current to said electric heater element, a thermostatic switch in said circuit for breaking said circuit when the heater block reaches a predetermined temperature, said switch having a re-set plunger which when operated re-establishes the circuit to said heater, and a lever member rockably mounted on said base bottom wall for actuating said re-set member, said actuating member projecting through said base for manual operation thereof.

DETAILED DESCRIPTION

Figure 1:
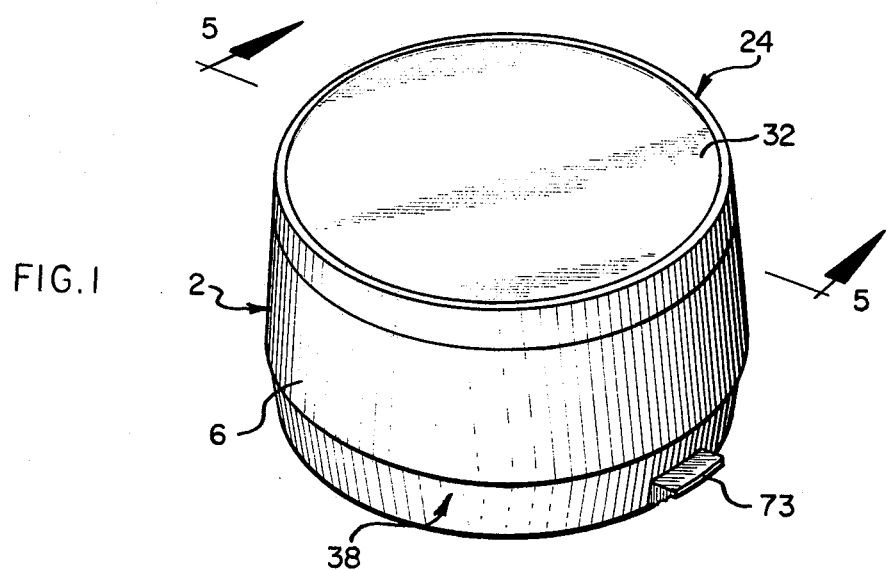
FIG. 1 is a perspective view of a sterilizer constructed in accordance with and embodying the present invention.
Figure 2:
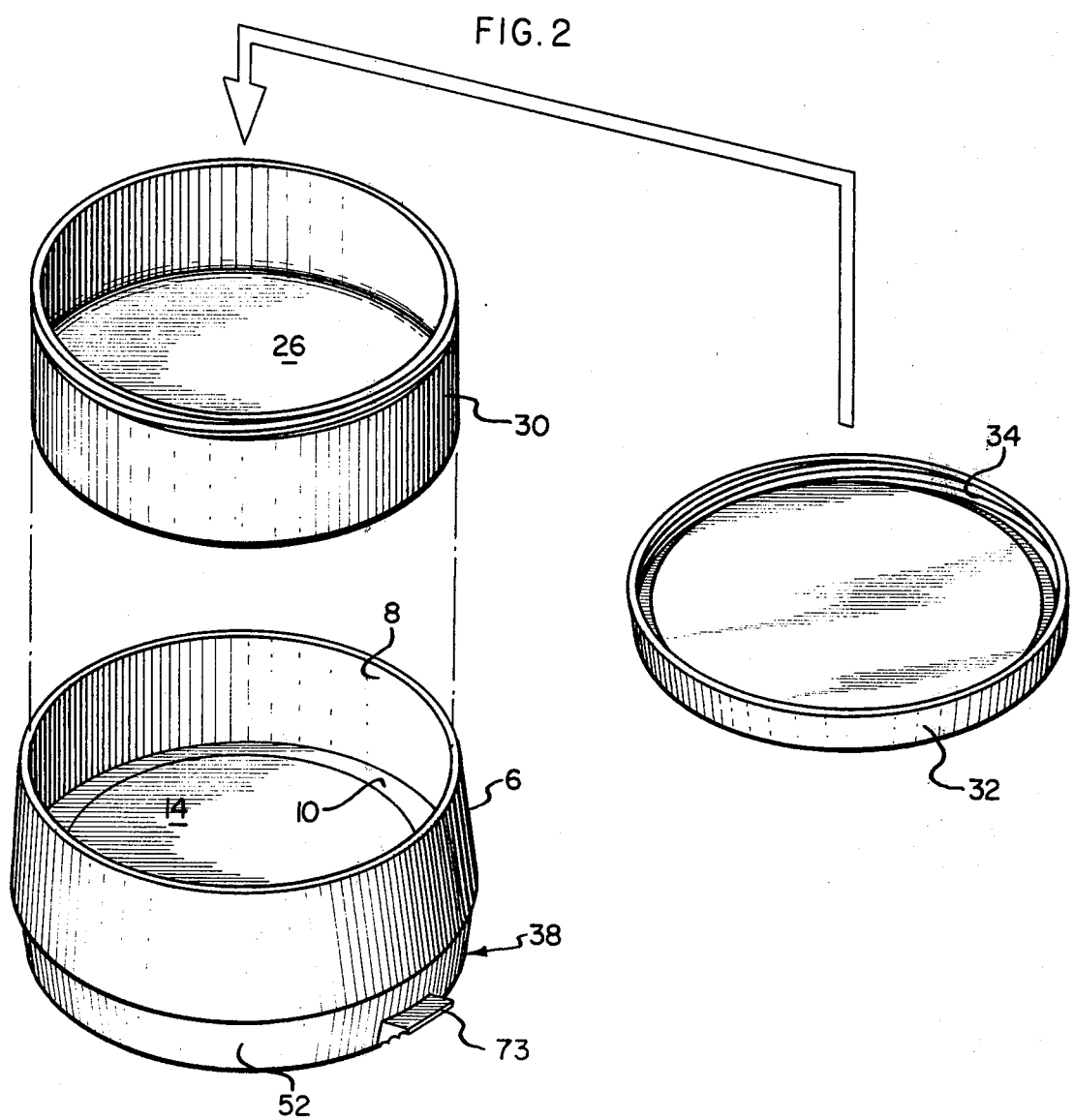
FIG. 2 is an exploded perspective view of the sterilizer.
Figure 3:
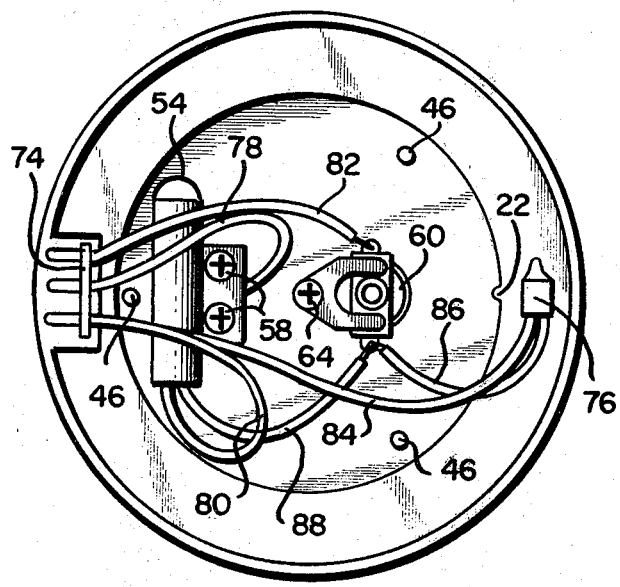
FIG. 3 is a bottom plan view of the sterilizer with the bottom cover thereof removed.
Figure 4:
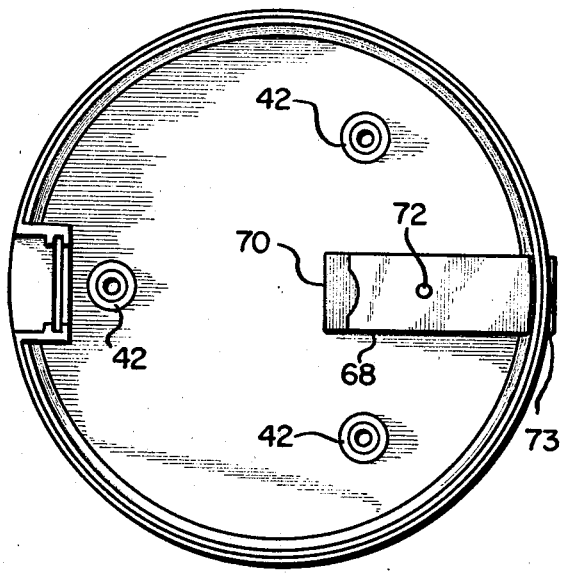
FIG. 4 is a top plan view of the bottom cover shown with the actuating lever mounted thereon.
Figure 5:
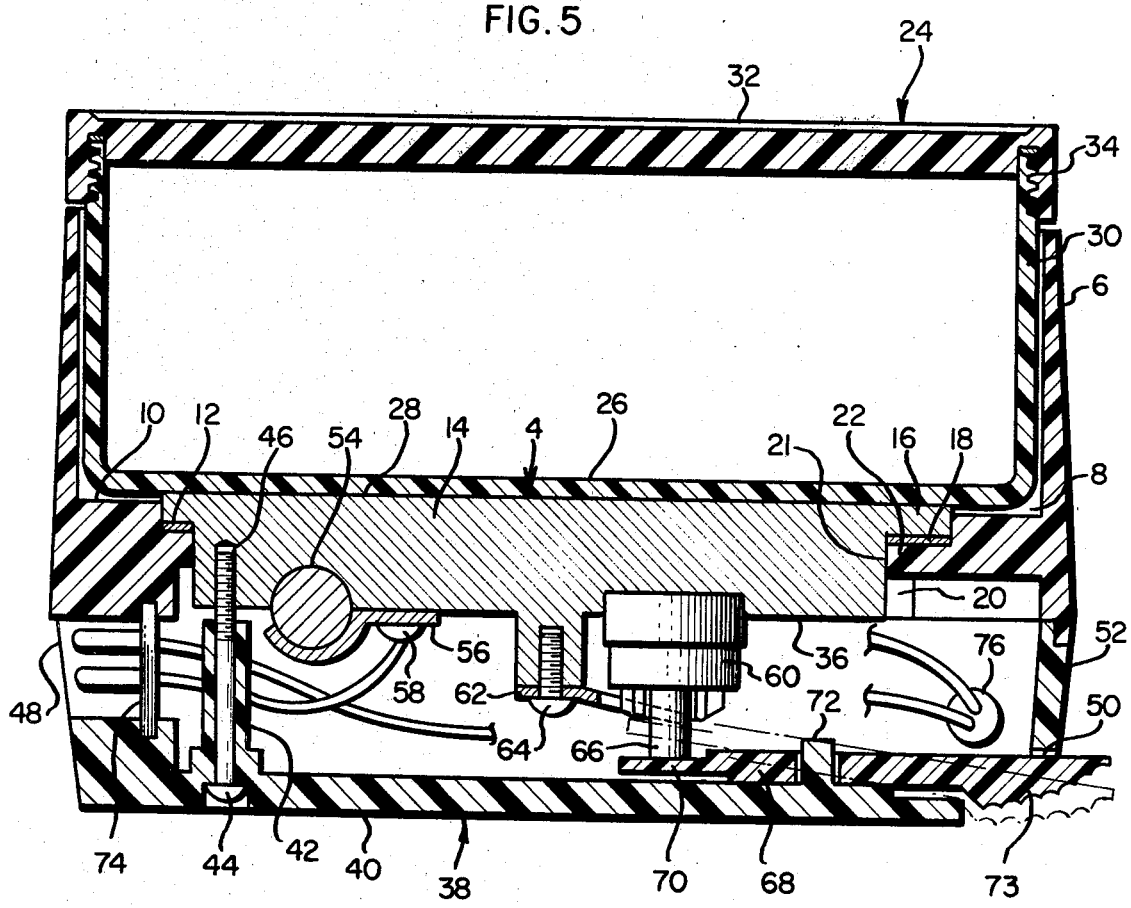
FIG. 5 is an enlarged sectional view taken along line 5—5 of FIG. 1.

Referring now in more detail to the drawing there is shown a device for sterilizing false teeth and the like comprising a base 2 having an intermediate support wall 4 and an annular upstanding sidewall 6 that cooperates with the support wall 4 to define an open top cavity 8. The sidewall 6 is formed of plastic as is an inwardly directed annular ledge 10 that forms part of the support wall 4 and includes a step 12. The inner diameter of the step 12 defines an opening 21 that receives a heater block 14, as best seen in FIG. 5. The heater block 14 may be of aluminum and has an upper annular flange 16 that is received by the step 12. The underside of the flange 16 may be provided with a resilient sealing gasket 18. At one region on its periphery the heater block 14 may be formed with an axial groove 20 that receives a key portion 22 of the step 12, whereby the heater block 14 may be properly oriented with respect to the remainder of the base during assembly of the device. Thus, the intermediate support wall 4 of the base 2 is a composite comprised of the heater block 14 and the ledge 10.

Provided for disposition within the cavity 8 is a plastic receptacle 24 having a flat lower end wall 26 which is adapted to seat on the flat upper surface 28 of the heater block 14. The receptacle 24 also has an annular sidewall 30 that telescopes with the base sidewall 6 and projects upwardly and outwardly therebeyond. Receptacle 24 also has a plastic cover 32 with an internal thread 34 that threads onto the upper end of the sidewall 30. The receptacle 24 is sized to accommodate the dentures to be sterilized or disinfected plus a quantity of sterilizing solution. Heat is transferred to the interior of the receptacle 24 and the disinfecting solution (not shown) through the surface-to-surface contact between the wall 26 and the heater block 14.

As can best be seen in FIG. 5, the intermediate wall 4 and corresponding heater block 14 are spaced from the bottom of the base 2. More specifically, the opposite or lower surface 36 the heater block 14 is positioned to receive or accommodate certain operating components of the device. This bottom surface 36 plus the wiring and components are covered by a plastic bottom cover member 38 having an end or bottom wall 40 that is spaced from the heater block surface 36. This bottom cover 38 integrally includes upstanding bosses 42,42,42 that receives screws 44 which thread into openings 46,46,46 in the heater block 14. The bosses 42,42,42 also serve to space the heater block 14 from the bottom wall 40. The air space between heater block 14 and bottom wall 40 serving to dissipate heat and insulate the bottom wall 40 from the heater components. When the bottom cover 38 is assembled with the base 2, the sidewall 52 of the bottom cover 38 edgewise engages the lower periphery of the sidewall 6, and there is provided a side opening 48 for the power terminal and a diametrically opposed opening 50 in the region of juncture of the bottom or end wall 40 and the sidewall 52 for the actuator lever, as will be discussed. Inlaid or recessed within the heater block 14 at the surface 36 is a conventional electric cartridge type heater 54 which supplies heat to the metal heater block 14. The heater 54 may be held in place by a clamp 56 that is secured to the heater block 14 and by screws 58.

Spaced from the heating element 54 is a thermostatic switch 60 which is also recessed in the heater block 14 at the surface 36 thereof. This switch 60 is held in place by a bifurcated clamp 62 that is secured to a central boss in the heater block 14 by a screw 64. The thermostatic switch 60 includes an axially shiftable re-set plunger 66 that projects toward the bottom wall 40, terminating in spaced relationship thereto. The recessing of the switch 60 into the heater block 14 assures that the thermostatic switch will reliably monitor the temperature of the heater block 14. Rockably mounted on the interior surface of the bottom wall 40 is an actuating lever 68 that is formed to a relatively flat configuration. This lever 68 has an end portion 70 which underlies the reset plunger 66 and is adapted to depress the plunger 66 axially upon movement of the lever 68 from the position shown in full lines in FIG. 5 to that shown in broken lines in FIG. 5. It will be seen that the lever 68 has a hole intermediate its ends for receiving an upstanding pin 72 formed on the bottom wall 40, whereby the lever 68 is somewhat loosely yet rockably mounted on the endwall 40 so as to utilize the bottom wall 40 as a fulcrum. The other end 73 of the lever 68 projects outwardly of the bottom cover 38 through the opening 50 for manual actuation by the user, thereby enabling the user to shift the lever to the broken line position shown in FIG. 5 to re-set the thermostatic switch 60, after it has functioned to terminate a previous heating cycle. At the opening 48 there is a terminal board unit 74 clinched between the ledge 10 and the bottom cover 38. The unit 74 receives a power supply receptacle of conventional construction for supplying current to the heater and to an indicator lamp 76. The central terminal of the unit 74 has a wire 78 connected to ground; the other two terminals are connected to the power line. These two terminals of receptacle 74 are connected to wires 80,82,84 which supply current to the heater element 54 and lamp 76 through the thermostatic switch 60. Wires 86,88 are respectively connected to the lamp 76 and to heater 54, and wires 86, 88 are connected to each other at one of the thermostatic switch terminals. Wire 82 is connected to the other thermostatic switch terminal, thus, the heater 54 and the lamp 76 are in parallel across the power line while the switch 60 is in series with each of the heater and lamp.

When the thermostatic switch 60 is below a predetermined temperature, current will be supplied to the heating element 54 and the current will also be supplied to the indicating lamp 76. However, when the thermostat senses a temperature above a predetermined valve thus indicating that the contents within the receptacle 24 have been heated to the desired temperature, the thermostatic switch opens, breaking the circuit to the heating element 54 and breaking the circuit to the indicator lamp 76. Upon opening of the switch 60, the re-set plunger is urged to the full line position of FIG. 5, and engages against the end 70 of the lever 68. The opposite end 73 of the lever 68 extends outwardly of the opening 50 for engagement by the operator should he or she desire to re-set the switch 60 and energize the heater. As a further matter the indicator lamp 76 is in close proximity to the lever end 73, which lever is transparent, such that the end 73 may be scalloped or otherwise contoured on its outer surface to provide reflecting or lenticular surfaces so that a visual indication is provided as to whether or not the lamp is illuminated and power is being supplied to the heater. When the lamp is extinguished it will signal that the cycle of operation of the sterilizer has been completed. Subsequently the thermostatic switch may be re-set by simply pressing down on the lever end 73 to operate the plunger 66 and switch 60.

Accordingly, while there has been disclosed a preferred form of the invention, it is contemplated that those skilled in the art may devise various modifications. In fact, it is intended that said modifications be covered as a part of the present invention, if they fall within the spirit and scope of the claims appended hereto.

What is claimed is:

1. A false teeth sterilizer comprising: a base member including, a cavity defined by an intermediate support wall and a surrounding sidewall, said cavity opening at the top of the base, said base member further including a bottom wall spaced from said intermediate support wall to define a substantially closed chamber therebetween, said intermediate wall being partially defined by a heater block for supplying heat to said cavity, which heater block includes a first relatively flat surface portion facing into said cavity and a second, oppositely disposed, surface portion facing into said chamber; a receptacle for receiving the false teeth to be sterilized, said receptacle being removable from said cavity and comprising a lower wall seated against the first surface portion of said heater block and a sidewall in telescoping relationship with said base sidewall, the receptacle sidewall projecting upwardly through said opened top, said receptacle having a corresponding opened top and a removable cover; an electrical heating element for said heater block disposed in said chamber and engaged against said second, oppositely disposed, surface portion of the heater block; circuit components also disposed within said chamber for supplying current to said heating element and including a thermostatic switch in circuit with said heating element and disposed in said chamber and engaged against said second oppositely disposed surface portion of said heater block at a location spaced from said electrical heating element, said thermostatic switch being capable of breaking the flow of current to said electrical heating element when the heater block reaches a predetermined temperature, said thermostatic switch including a reset plunger within the chamber and extending toward said base wall, but spaced from said base wall, which plunger when operated is capable of reestablishing the flow of current to said electrical heating element, a lever member rockably mounted on an interior surface of said bottom wall and including a first end portion disposed between said plunger and said bottom wall, said lever including an opposite end projecting outwardly and exteriorially of said base member, such as said lever member may be depressed and rocked to cause said first end portion to engage and actuate said reset plunger.

2. A device according to claim 1 in which a pin projects upwardly from said bottom wall and loosely through said lever to retain the lever assembled with said bottom wall.

3. A device according to claim 1, wherein an indicator lamp is included in said circuit and disposed in close proximity to said lever, said lever being transparent and capable of transmitting the light from said lamp to provide a visual indication when said circuit is energized.

* * * * *